(12) United States Patent
Yang et al.

(10) Patent No.: US 7,427,509 B2
(45) Date of Patent: Sep. 23, 2008

(54) METHOD AND APPARATUS FOR MEASURING FLUORESCENCE POLARIZATION IN LAB-ON-A-CHIP

(75) Inventors: Eun Gyeong Yang, Seoul (KR); Jung Hwan Kim, Incheon-si (KR); Tae Song Kim, Seoul (KR); Byeong-Kwon Ju, Seoul (KR); Ji Yoon Kang, Seoul (KR); Hyun Joon Shin, Seoul (KR); Han-Sang Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 11/422,142

(22) Filed: Jun. 5, 2006

(65) Prior Publication Data

US 2007/0117220 A1  May 24, 2007

(30) Foreign Application Priority Data

Nov. 23, 2005  (KR)  ...................... 10-2005-0112165

(51) Int. Cl.
*G01N 21/76* (2006.01)
(52) U.S. Cl. ...................................... 436/172; 356/364
(58) Field of Classification Search ................. 436/172, 436/164, 800, 805, 514; 356/346, 303, 244, 356/246, 364; 435/6, 7.1
See application file for complete search history.

(56) References Cited

U.S. PATENT DOCUMENTS 4,626,684 A * 12/1986 Landa ......................... 250/328
5,427,915 A * 6/1995 Ribi et al. ................... 435/7.92
5,641,629 A * 6/1997 Pitner et al. ..................... 435/6
6,410,255 B1 * 6/2002 Pollok et al. .................. 435/23
6,458,259 B1 * 10/2002 Parce et al. .................. 204/454
6,846,638 B2 * 1/2005 Shipwash .................... 435/7.1
2002/0158212 A1 * 10/2002 French et al. ............. 250/459.1

OTHER PUBLICATIONS

Wan and Le, "Studies of Protein-DNA Interactions by Capillary Electrophoresis/Laser-Induced Fluorescence Polarization," Analytical Chemistry, 72(22): 5583-5589 (2000).
Yadavalli and Pishko, "Biosensing in Microfluidic Channels Using Fluorescence Polarization," Analytica Chimica Acta, 507: 123-128 (2004).

* cited by examiner

*Primary Examiner*—Ann Y Lam
(74) *Attorney, Agent, or Firm*—Joseph Hyosuk Kim; JHK Law

(57) ABSTRACT

Disclosed relates to a method and an apparatus for measuring fluorescence polarization FP in a lab-on-a-chip and, more concretely, to a method and an apparatus that measure quantitatively interactions between biomolecules and fluorescently labeled biomaterials and enzyme activities using the measurement of fluorescence polarization FP. The method and the apparatus of the invention provide rapid assays with minute amounts of samples using an automated device compared to conventional methods. Accordingly, the method and the apparatus of the invention can be usefully applied to the measurement of interactions between biomolecules and to the protease assays using a protein substrate.

12 Claims, 9 Drawing Sheets

METHOD AND APPARATUS FOR MEASURING FLUORESCENCE POLARIZATION IN LAB-ON-A-CHIP

BACKGROUND OF THE INVENTION

1. Field of the Invention

The present invention relates to a fluorescence polarization measurement system in a lab-on-a-chip and, more particularly, to a method and an apparatus for measuring fluorescence polarization FP in a lab-on-a-chip that analyze quantitatively interactions between minute amounts of biomolecules using fluorescence polarization, and a method for detecting a substance that induces or inhibits formation of a complex of biomolecules using the method for measuring fluorescence polarization in a lab-on-chip.

2. Description of Related Art

A fluorometry that measures fluorescence provides one of the important methods in bioassay techniques. The fluorometry includes fluorescence intensity, fluorescence fluctuation spectroscopy, fluorescence imaging, fluorescence resonance energy transfer (FRET), and fluorescence polarization FP. Due to its sensitive nature, the fluorometry has been continuously substituted for assay methods using radioactive isotopes.

Among these, fluorescence polarization FP, the concept of which was introduced by Perrin, is directed to a method of measuring the time-averaged rotation motion of a fluorescent molecule. Therefore, the measurement of fluorescence polarization FP is based on the principle that a fluorescent molecule generates FP when it does not rotate in excited state, whereas a fluorescent molecule emits fluorescence in all planes, resulting in loss of FP, when it rotates freely by Brownian motion in the excited state.

The method for measuring fluorescence polarization FP has been acknowledged as a powerful and unique method in analyzing interactions between molecules. Fluorescence polarization FP is generally inversely proportional to rotation time of molecules and influenced by absolute temperature, and molecular viscosity and volume. Such method provides a direct assay that does not require a solid phase separation and is capable of measuring interactions between fluorescently labeled biomaterials and other biomolecules with high sensitivity, owing to the relation of FP to changes in molecular size. That is, the method analyzes interactions between biomaterials based on the principle that when the net molecular volume increases due to the binding of small fluorescently labeled biomaterials with other biomolecules, fluorescence polarization FP increases, whereas, when the molecular volume decreases due to biomolecules' separation, FP also decreases.

A system for measuring fluorescence polarization FP is configured generally in a manner that when monochromatic light passing through a polarizer excites fluorescent molecules in a sample tube, only molecules oriented toward the same polarized plane as the irradiating light absorb the light to be excited. Then, the light emitted from the excited molecules is measured in both vertical and horizontal planes.

The values of fluorescence polarization FP that express how much the molecules rotate during excitation and emission are calculated according to:

$$FP = (I_{VV} - I_{VH}G)/(I_{VV} + I_{VH}G)$$

wherein $I_{VV}$ represents a vertical fluorescence intensity; $I_{VH}$ denotes a horizontal fluorescence intensity; and G (G-factor; $I_{VV}/I_{VH}$) is an empirical constant that corrects for the polarization bias introduced by the optics and the detection system. To apply the method for measuring fluorescence polarization FP to mass analyses, scanning methods based on the principle of fluorescence microscopy are generally used for the samples processed in well plates. The amount of the sample used is about 100 μL in case of a 96-well plate and about 40 μL in case of a 384-well plate.

A system for measuring fluorescence polarization FP used on capillary electrophoresis has been reported to involve separation of a biomolecular complex via capillary electrophoresis and collection of the separated complex using a cuvette cell to measure the fluorescence intensities in both vertical and horizontal planes, thus obtaining fluorescence polarization. Since the system described above comprises two steps of separating and measuring and uses a relatively large cuvette cell (0.2 mm×0.2 mm), it has a drawback in collecting a considerable amount of separated biomolecules for the large cuvette cell [Anal. Chem. 72(2000) pp. 5583-5589].

The use of fluorescence polarization FP, on the other hand, has not been extensively explored for applications in lab-on-a-chip devices although it serves as a valuable technique for analyses of biomolecular interactions in conventional well-plate formats and by capillary electrophoresis. Only very recently, biosensing of homogeneous molecular binding by FP detection using a commercial fluorescence spectrometer has been attempted in relatively large plastic microchannels [Anal. Chim. Acta 507 (2004) pp. 123-128].

The system using the above plastic channel mixes an analytic solution with fluorescently labeled antibody/enzyme in a reservoir to form a complex. Then, the complex flows in a plastic channel having a diameter of 300 μm to 500 μm, which is made of poly dimethyl Siloxane PDMS Block. The channel containing samples is irradiated with polarized light, and the emitted fluorescence is measured on a conventional spectrometer to yield fluorescence polarization FP as shown in FIG. 1.

Here, substances mix in the reservoir flow in a disposable plastic channel having a larger diameter of 300 μm to 500 μm to be measured by the conventional fluorescence spectrometer. Although the measurement can be readily carried out, it requires a considerable volume of about 10 μL and also a good many quantity of 10 nmol to 40 nmol of samples. In addition, the use of the disposable plastic channel has some drawbacks in that it is difficult to monitor the reaction of continuously flowing samples, and to measure the fluorescence signals due to large background signals in a miniaturized microchannel.

Meanwhile, a lab-on-a-chip is a kind of biochip integrating various devices for sample preparation, sample injection, reaction, separation, measurement and the like on a substrate having a size of several square centimeters and made of glass, silicon or plastic using a technique of photolithography used in fabricating semiconductors. That is, the lab-on-a-chip means a physical, chemical and biological microprocessor that a laboratory is put on. The lab-on-a-chip includes a microchannel made of plastic, glass, silicon or the like, through which samples of nanoliters or less are tested. Accordingly, various experiments performed in existing laboratories can be executed in such a lab-on-a-chip and it is possible to carry out automated experiments at a high speed, and with high efficiency and low cost using the lab-on-a-chip.

Especially, the lab-on-a-chip has attracted attention as a next-generation diagnostic apparatus as biotechnologies have rapidly developed since the year 2000. Using this chip, only a drop of blood would be enough to diagnose various cancers or measure the number of erythrocytes and leukocytes. In addition, the lab-on-a-chip is a higher value-added product that can expand its application into numerous fields such as stock breeding, environment, etc.

However, a high-throughput analysis system for measuring fluorescence polarization FP in a lab-on-a-chip has not been well known. With this system, it is possible to execute an interaction analysis by fluorescence polarization FP with high sensitivity using a minute amount of a sample.

Various techniques on identification and quantification of the activity of proteolytic enzyme have been developed, including measurements of absorbance or fluorescence liberated in the supernatant of precipitation assay, homogeneous fluorometric assays using fluorescence-quenched, hyperconjugated fluorescein derivatives of protease substrates, and fluorescence polarization FP based assays of fluorescently labeled-protein substrate. The former suffers from the need for careful sampling intervals, control of sample volumes, and separation of labeled hydrolysis products from unhydrolyzed protein, while the latter two appear to provide a rapid and convenient measurement system. Since fluorescence polarization FP is independent of fluorescence intensity and thus more tolerant of fluorescence intensity fluctuations, it is possible to measure the activities of various proteases sensitively by the fluorescence polarization FP based assays.

The existing assay method for the activity of protease is to use a fluorescently labeled peptide substrate for a specific protease. But the method has a problem in that it needs specific substrates for the respective proteases. Accordingly, the assay system for the activities of proteases in a lab-on-a-chip using fluorescence polarization FP and a universal protein substrate, which will be described hereinafter in various embodiments of the present invention, is generally applicable to various proteases.

The inventors of the present invention have tried to develop a system for measuring fluorescence polarization FP in a lab-on-a-chip using a sample of several pmol to several tens of fmol, and completed a method and an apparatus for measuring fluorescence in a lab-on-a-chip of the present invention that analyze quantitatively interactions between biomolecules and fluorescently labeled biomaterials, and a method for detecting a substance that induces or inhibits formation of a complex of biomolecules using the method for measuring fluorescence polarization FP in a lab-on-a-chip.

SUMMARY OF THE INVENTION

Accordingly, an object of the present invention is to provide a method for measuring fluorescence polarization FP in a lab-on-a-chip that analyzes quantitatively interactions between biomolecules and fluorescently labeled biomaterials.

Moreover, another object of the present invention is to provide a method for detecting a substance that induces or inhibits formation of a complex of biomolecules or a method for measuring activity or concentration of enzymes using the method for measuring fluorescence polarization.

In addition, a yet another object of the present invention is to provide a fluorescence polarization FP measuring apparatus for a microchannel.

According to the fluorescence polarization FP measuring apparatus for a microchannel of the present invention, when a polarized light is irradiated to a microchannel, in which the flowing samples are targeted for measurement, a fluorescent substance is excited to generate fluorescence. Then, the generated fluorescence is measured in the same direction as fluorescence is radiated and in a vertical direction to calculate fluorescence polarization, thus analyzing the status of molecular binding in the samples. The method of the present invention can be adopted to measure quantitatively interactions between biomolecules and fluorescently labeled biomaterials, or between biomolecules.

The method for measuring fluorescence polarization FP in a lab-on-a-chip comprises the steps of:

(1) preparing a fluorescently labeled biomaterial and a biomolecule;

(2) injecting the fluorescently labeled biomaterial and the biomolecule into a microchannel of a lab-on-a-chip to form a complex;

(3) irradiating a polarized light to the complex to measure fluorescence polarization FP; and (4) quantifying fluorescence polarization to determine the extent of fluorescence polarization.

The lab-on-a-chip is made of glass by standard semiconductor photolithographic techniques and has a width and a length of 1 cm to 10 cm, respectively. The microchannel of the lab-on-a-chip has a depth of 5 μm to 150 μm, a width of 10 μm to 300 μm and a length of 10 mm to 100 mm. In the present invention, it is desirable to use a microchannel having a width of 10 μm to 100 μm. Here, the glass chip can provide successive injection measurements in high sensitivity since it has relatively less absorption problems.

The lab-on-a-chip includes a thin microchannel and is designed in a manner that physical, chemical and biological experiments for reactants are carried out at both ends and inside thereof to obtain desired results as depicted in FIG. 3A.

The lab-on-a-chip comprises a reservoir 1 for storing fluorescently labeled biomaterials; a reservoir 2 for storing biomolecules; a well plate 3 containing a sample material; a capillary supplier 4 for injecting the sample material therein; a detection point 5 for detecting fluorescence polarization FP; and a vacuum pump and a waste reservoir 6 for forcing the sample material into a main channel thereof. Here, two channels from the two reservoirs 1 and 2 meet with the main channel in the middle thereof. One end of the main channel has a capillary tube, through which the sample material is injected into the main channel, and the other end of the main channel has a waste reservoir 6 for gathering reactants by the pressure gradient generated using the vacuum pump 6.

The methods of the invention described above will be described in steps hereinafter.

In step (1), fluorescently labeled biomaterials are stored in the reservoir 1 and biomolecules to be bound with the fluorescently labeled biomaterials are stored in the reservoir 2 as depicted in FIG. 3A. The biomolecules generally have much larger molecular volumes than the fluorescently labeled biomaterials, and various kinds of biomolecules such as protein, hexane and the like are applicable. The fluorescently labeled biomaterials have much smaller molecular volumes than the biomolecules, and fluorescent probe molecules such as tetramethylrhodamine TMR are utilized to produce fluorescently labeled biomaterials.

In step (2), the biomolecules and the fluorescently labeled biomaterials meet with the main channel via a microfluidic control by the pressure gradient generated using the vacuum pump on top of the waste reservoir 6. Here, it is desirable to set the fluid flow velocity at about 1 nl/sec. Fluorescence polarization FP is detected at the detection point 5 provided on the main channel. Here, the formation of the complex of biomolecule and fluorescently labeled biomaterial is completed prior to the measurement. The formation of the biomolecule-fluorescently labeled biomaterial complex varies as the kind and the concentration of the component molecules of the complex and the buffer solution. In addition, according to pH values, a stable complex can be formed or not.

In step (3), after irradiating a polarized light to the biomolecule-fluorescently labeled biomaterial complex in the microchannel of the lab-on-a-chip, excited fluorescence passes through vertical and horizontal photomultiplier tubes and these measured values are used to calculate fluorescence polarization FP.

Here, to obtain a G-factor value, which is a compensation value of a fluorometer and a light source for a specific probe used for derivatizing a fluorescently labeled biomaterial, a dilute solution of the probe is filled in the microchannel of the lab-on-a-chip, onto which light is irradiated to be excited with a polarizer detached. Then, the fluorescence that passes through the vertical and horizontal photomultiplier tubes is measured and these fluorescence intensities are used to calculate the G-factor value.

In addition, for the measurement of fluorescence polarization FP of the minute amounts of samples in the microchannel of the lab-on-a-chip, it is necessary to improve the signal-to-noise ratio by separating a specific frequency signal before the light source for the irradiation of polarized light passes through the polarizer. For this purpose, an optical chopper composed of a slotted rotating disc is adopted to separate a specific frequency signal.

In step (4), fluorescence polarization FP is measured from the G-factor value and the measured vertical and horizontal fluorescence values, i.e., the electric current signals converted from optic signals by passing through the photomultiplier tube PMT which are detected by oscilloscopes to determine the extent of fluorescence polarization.

Furthermore, the present invention provides a method for detecting a substance that induces or inhibits formation of a complex of biomolecules or a method for measuring activity or concentration of enzymes using the method for measuring fluorescence polarization FP.

The detection method of the invention is directed to a process for detecting a substance that inhibits formation of a complex of biomolecules by observing the decrease of fluorescence polarization FP due to a competing reaction against the formation of the complex of biomolecules, or to a process for detecting a substance that induces formation of a complex of biomolecules by observing the increase of fluorescence polarization FP. In addition, according to the method for measuring the activity or the concentration of enzymes using the method for measuring fluorescence polarization FP, the activity or the concentration of enzymes can be measured by observing the variation of fluorescence polarization FP after the reaction of a biomolecule substrate bound with the fluorescent probe by an enzyme. The enzyme is preferably a protease and, more preferably, proteinase K, trypsin, papain or elastase. Besides, casein is preferably used as a universal protein substrate. In case of using casein as a substrate, it is possible to analyze the proteases readily since there is no need to change the substrates suitable for the respective proteases.

The detection method of the invention using the method for measuring fluorescence polarization FP in a lab-on-a-chip comprises the steps of:

(1) preparing a fluorescently labeled biomaterial and a biomolecule;

(2) injecting the fluorescently labeled biomaterial and the biomolecule into a microchannel in a lab-on-a-chip to form a complex;

(3) causing a reaction between the complex and a sample material;

(4) irradiating a polarized light to the resultant complex to measure fluorescence polarization FP; and (5) quantifying the measured fluorescence polarization FP to determine the extent of fluorescence polarization.

The lab-on-a-chip comprises a reservoir 1 for storing fluorescently labeled biomaterials; a reservoir 2 for storing biomolecules; a well plate 3 containing a sample material; a capillary supplier 4 for injecting the sample material therein; a detection point 5 for detecting fluorescence polarization FP; and a vacuum pump 6 for forcing the sample material into a main channel thereof. Here, two channels from the two reservoirs 1 and 2 meet with the main channel in the middle thereof. One end of the main channel has a capillary tube, through which the sample material is injected into the main channel, and the other end of the main channel has a waste reservoir for gathering reactants by the pressure gradient generated using the vacuum pump 6.

Steps (1) and (2) are executed in the same manner as those of the method for measuring fluorescence polarization FP described above. In step (3), the sample material is put into the well plate 3 to react with the complex in turn or in parallel using the capillary supplier 4 for injecting the sample material into the chip. In this step, the sample material denotes a detection target substance or an enzyme.

In steps (4) and (5), fluorescence polarization FP of the resultant complex is measured in the same manner described above to determine how much the sample material induces or inhibits the formation of the complex, or to measure the activity or the concentration of enzymes.

FIG. 3B shows an expected diagram for signals to be measured at the detection point of the microchannel: wherein A denotes a case that fluorescence polarization FP is shown as small since only the fluorescently labeled biomaterials are injected into the main channel; B represents a case that fluorescence polarization FP is shown as larger, since the fluorescently labeled biomaterials and the biomolecules are injected into the main channel to form a complex; and C expresses a case that fluorescence polarization FP becomes smaller again, since an inhibitor reacts to bind with biomolecules instead of the fluorescently labeled biomaterials by competition.

The method for measuring fluorescence polarization FP, the detection method using the same and the method for measuring the activity or the concentration using the same in accordance with the present invention stores two substances for the measurement in reservoirs of a lab-on-a-chip to be injected into a microchannel by the pressure gradient generated using a vacuum pump, thus readily confirming the binding state of the substances and whether the substances induce or inhibit the formation of the complex. Accordingly, the methods described above may be applied usefully to the measurement of the substances that induce or inhibit the formation of the complex of biomolecules or the activity or the concentration of enzymes using the method for measuring fluorescence polarization FP.

Moreover, the present invention provides a fluorescence polarization measuring apparatus for a microchannel. In the apparatus, a fluorescent reactant is injected into a microchannel and a polarized light is applied to the reactant, thus quantitatively measuring interactions between biomolecules and fluorescently labeled biomaterials, or between biomolecules.

The fluorescence polarization measuring apparatus for a microchannel comprises a polarization generation part, a fluorescence polarization separation part and a fluorescence polarization measurement part.

A detailed configuration of the apparatus will be described hereinafter with reference to FIG. 2.

The polarization generation part includes:

a laser source;

a first filter that filters light emitted from the laser source;

first and second mirrors that control the direction of the light passing through the first filter;

a polarizer that polarizes the light reflected by the second mirror;

a beam splitter that splits the polarized light passing through the polarizer; and a lens that collimates the polarized light to the sample material in the microchannel.

The fluorescence polarization separation part includes:

a lens that collects fluorescence emitted by excited fluorescently labeled biomaterials by polarized light irradiated from the polarization generation part;

a third mirror that controls the direction of the fluorescence passing through the lens;

a second filter that filters the fluorescence reflected by the third mirror; and a polarized beam splitter that splits the fluorescence passing through the second filter.

The fluorescence polarization measurement part includes:

a third filter that filters the fluorescence passing through the polarized beam splitter;

vertical and horizontal photomultiplier tubes (PMTs) that measure fluorescence signals of the emitted light passing through the third filter in vertical and horizontal planes;

a polarizer installed in front of the horizontal PMT; and an oscilloscope that measures the fluorescence polarization passing through the photomultiplier tubes (PMTs).

The vertical fluorescence signal is measured by the vertical PMT and the horizontal fluorescence signal by the horizontal PMT. Ideally, two PMTs should receive 100% vertical and horizontal fluorescence signals. However, 1% vertical fluorescence signal is mixed in the signal received by the horizontal PMT, while >99% vertical fluorescence signal is received by the vertical PMT. Accordingly, another polarizer installed in front of the horizontal PMT minimizes the vertical component mixed with the signal and increases the horizontal fluorescence content.

In addition, an optical chopper composed of a slotted rotating disc is placed between the first filter and the first mirror for turning on/off the light source periodically, which improves the signal-to-noise ratio, thus allowing the measurement of fluorescence polarization using minute amounts of samples possible in the narrow microchannel of the present invention.

The fluorescence polarization measuring apparatus for a microchannel may be applied usefully to the measurement of substances that induce or inhibit the formation of the complex between biomolecules or to the measurement of the activity or the concentration of enzymes in combination with the method for measuring fluorescence polarization FP in a lab-on-a-chip of the present invention described above.

The apparatus according to the invention requires about several tens of fmol of samples, such as fluorescently labeled biomaterials and biomolecules, assuming that the detection time required per substance is 20 seconds, which is a considerably smaller amount than the time required in the previously reported method for measuring fluorescence polarization FP using a plastic chip.

Furthermore, this invention allows cost reduction in analysis, when compared to a high-throughput analysis using a 384-well plate which requires about 4 pmol per sample.

Accordingly, the method and apparatus for measuring fluorescence polarization of the present invention configured to enhance the signal-to-noise ratio to increase sensitivity and reliability of measurements can readily measure interactions between biomolecules efficiently at low cost with a minute amount of samples, and be applied to an ultra-speed measurement aimed at such advantages.

DETAILED DESCRIPTION OF THE INVENTION

Hereinafter, preferred embodiments of the present invention will be described in detail with reference to the attached drawings. The present invention is not restricted to the following embodiments, and many variations are possible within the spirit and scope of the present invention. The embodiments of the present invention are provided in order to more completely explain the present invention to anyone skilled in the art.

COMPARATIVE EXAMPLE

Fluorescence polarization FP for the complex formation of TMR-biotin and streptavidin was measured in a 100 μL cuvette by a commercial fluorescence spectrometer (Perkin Elmer).

In this measurement, using phosphate-buffered-saline PBS as a buffer solution, fluorescence polarization FP was measured with measurements divided into two cases: (A) wherein only 1.25 μM of TMR-biotin was put therein; and (B) wherein 10 μM of TMR-biotin and 2.5 μM of streptavidin were put together therein.

Figure 4:
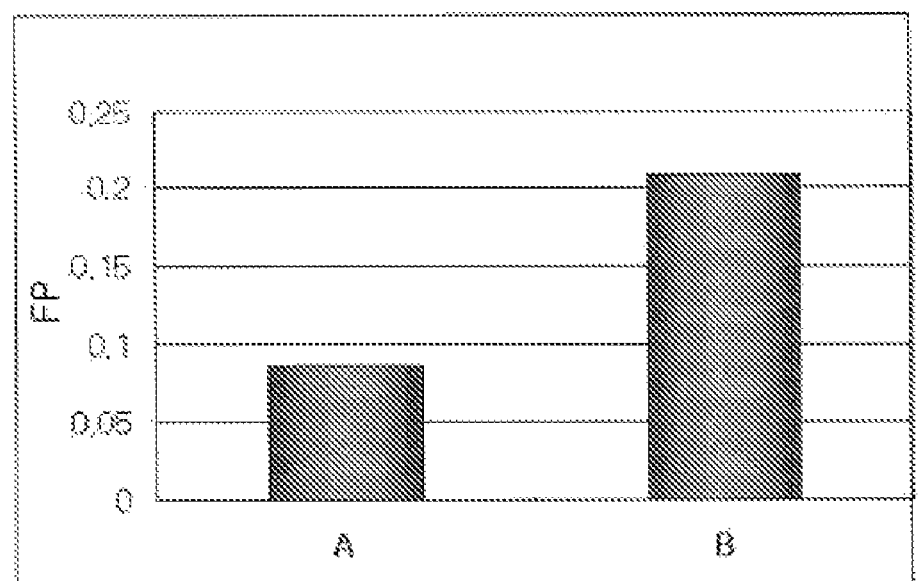
FIG. 4 is a graph showing fluorescence polarization FP for samples containing TMR-biotin only, and TMR-biotin mixed with streptavidin measured by a commercial fluorescence spectrometer (Perkin Elmer) in accordance with a comparative example of the invention.

In case of (A), fluorescence polarization FP was measured 0.086, and in case of (B), it was 0.209. Here, the slit width was 2.5 nm and the integration time was 1 second. As shown in FIG. 4, upon formation of a complex by mixing the above substances, the increase of fluorescence polarization FP was observed.

In addition, since it was observed that the fluorescence intensity was decreased by quenching when TMR-biotin formed a complex with streptavidin, TMR-biotin of (B) was used at an eight-fold higher concentration than that of (A) in order to minimize variations caused by changes in the fluorescence intensity. In order to use the same concentrations of fluorescent substances to be used in the chip for the measurement of fluorescence polarization, the slit width was adjusted to 2.5 nm and the integration time to 1 second.

EMBODIMENT 1

Figure 1:
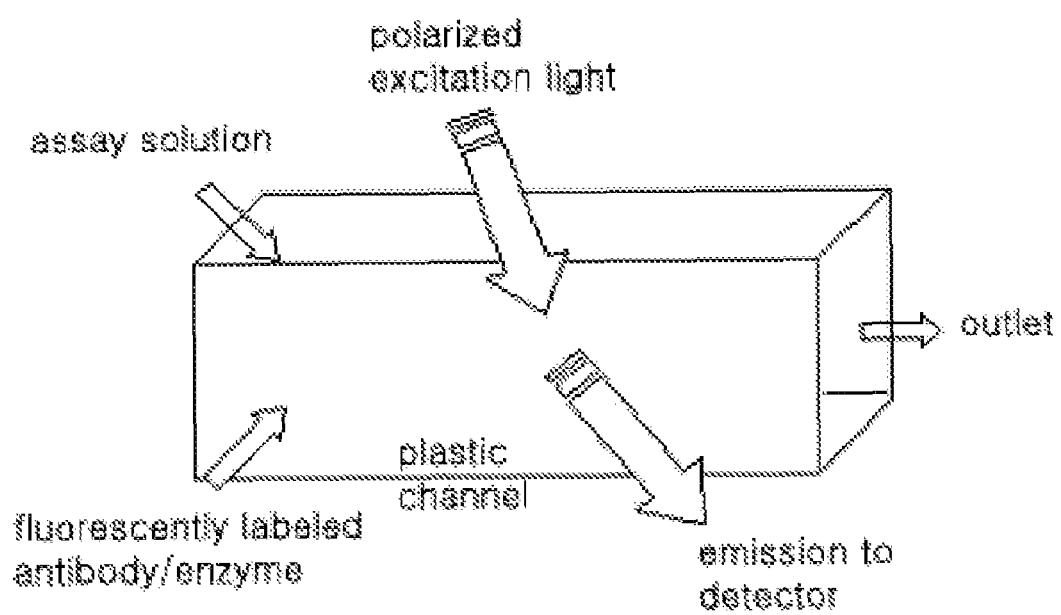
FIG. 1 is a conceptual diagram of a previously reported fluorescence polarization measurement in a plastic channel, wherein samples premixed in a reservoir flow, and fluorescence polarization is measured.
Figure 2:
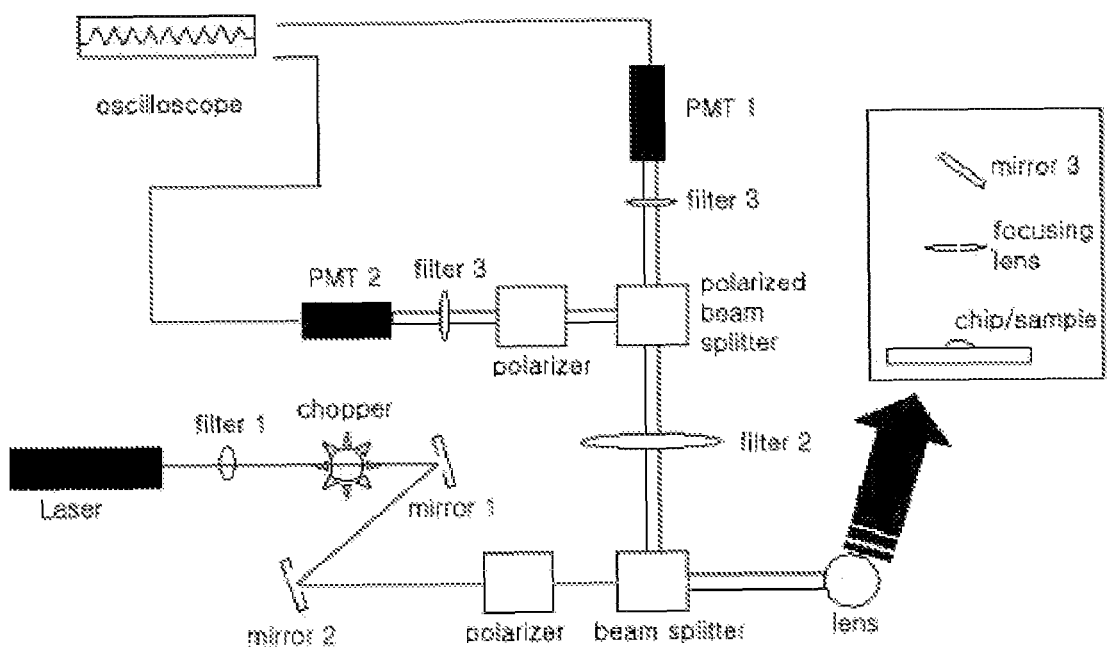
FIG. 2 is a diagram showing a configuration of an apparatus for measuring fluorescence polarization of samples continuously flowing in a microchannel of a lab-on-a-chip made of glass in accordance with an embodiment of the present invention.

Fluorescence polarization FP for the complex formation of biotin and streptavidin was measured in a 100 μL cuvette using an apparatus for measuring fluorescence polarization FP of FIG. 2, wherein an optical chopper was not inserted.

In this Embodiment, the measurements were carried out, and separately divided into three cases according to the respective samples used for the complex formation of biomolecule-fluorescently labeled biomaterial as follows (FIG. 5): (A) and (B), wherein only 1.25 μM of TMR was put therein; (C) and (D), wherein 1.25 μM of TMR-biotin was put therein; and (E) and (F), wherein 10 μM of TMR-biotin and 2.5 μM of streptavidin were put therein.

First, 100 nM of TMR used as a fluorescent probe for fluorescently labeled biomaterials was filled in the 100 μL cuvette of the lab-on-a-chip with the fluorescence polarization detection setup in FIG. 2, in which a polarizer was detached, and laser beam was irradiated to induce fluorescence. Then, the fluorescence passed through the vertical and horizontal photomultiplier tubes to obtain the G-factor value, which was a compensation value of a fluorometer and a light source for a specific fluorescent probe used in a fluorescently labeled biomaterial, from the fluorescence intensity. Subsequently, the polarizer was attached in place to irradiate a polarized light to the samples in the microchannel to be excited. The excited fluorescence passed through the vertical and horizontal photomultiplier tubes to measure fluorescence intensity of the vertically and horizontally polarized components, thus obtaining fluorescence polarization from the measured value and the G-factor value.

The apparatus used for the measurements in accordance with embodiment 1 comprises a polarization generation part, a fluorescence polarization separation part and a fluorescence polarization measurement part.

The polarization generation part includes:
a 543.5 nm laser source (5 mW maximum at 543.5 nm, brand name: Green Cylindrical Helium-Neon Laser, manufactured by Coherent);
a first filter for a wavelength of 543.5 nm having a diameter of 12.5 mm (brand name: Mounted Interference Filter, manufactured by Melles Griot);
first and second mirrors each having a diameter of 1" (inch) and a thickness of ⅜" (brand name: Enhanced Aluminum Mirror, manufactured by CVI);
a polarizer (brand name: Broadband Polarizing Beamsplitter Cubes, manufactured by CVI);
a beam splitter (brand name: Spectrally Neutral Cube Beamsplitter, manufactured by CVI); and
a lens system having a third mirror, the same one as the first and second mirrors, and a focusing lens (brand name: Precision Optimized Achromats, manufactured by Melles Griot).

A rotating disc optical chopper (brand name: 300D4/7, manufactured by SCITEC Instruments) containing outer seven slots and inner four slots was used.

The fluorescence polarization separation part includes:
a focusing lens having a diameter of 10 mm (brand name: Optimized Achromats, manufactured by Melles Griot) that collects fluorescence emitted by the TMR dye;
a third mirror, the same one as the first and second mirrors;
a second filter for a wavelength of 580 nm having a diameter of 50 nm (brand name: Mounted Interference Filter, manufactured by Melles Griot); and
a polarized beam splitter (brand name: Broadband Polarizing Beamsplitter Cube, manufactured by CVI).

The fluorescence polarization measurement part includes:
a third filter for a wavelength of 580 nm having a diameter of 1" (brand name: BK7 A Coated Plano Convex Lens, manufactured by Thorlab);
vertical and horizontal photomultiplier tubes (PMTS) that measure fluorescence signals in vertical and horizontal planes (brand name: H5784-01, manufactured by HAMAMATSU);
a polarizer installed in front of the horizontal PMT; and
an oscilloscope (brand name: Agilent 54642A 2Channel 500MHz Oscilloscope, manufactured by Agilent).

Figure 5:
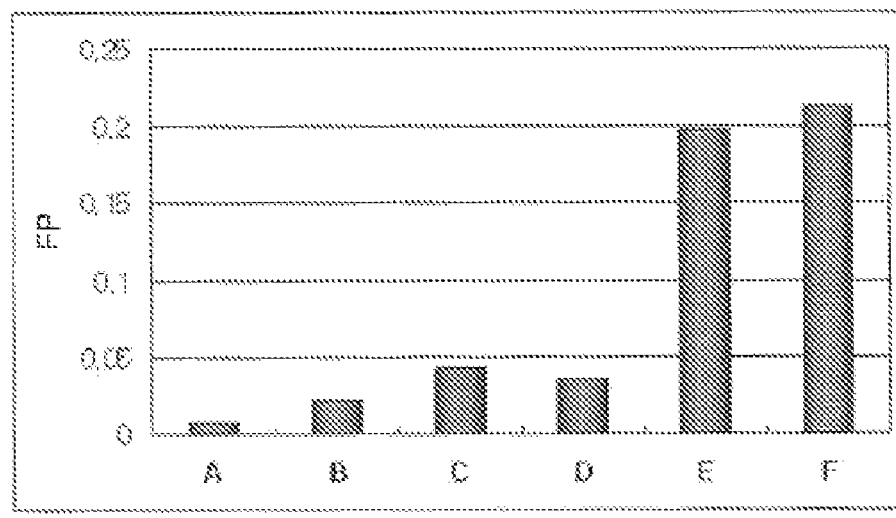
FIG. 5 is a graph showing fluorescence polarization FP for binding of fluorescently labeled biomaterials with biomolecules in a cuvette by the apparatus of FIG. 2, wherein an optical chopper is detached, in accordance with Embodiment 1 of the invention.

Here, the photomultiplier tube gain (PMT gain) was 0.6 V. In case of (A), fluorescence polarization was measured 0.007; in case of (B), it was 0.020; in case of (C), it was 0.043; in case of (D), it was 0.036; in case of (E), it was 0.197; and in case of (F), it was 0.213, which were increased as the complex of TMR-biotin and streptavidin was formed as shown in FIG. 5.

EMBODIMENT 2

Figure 3A:
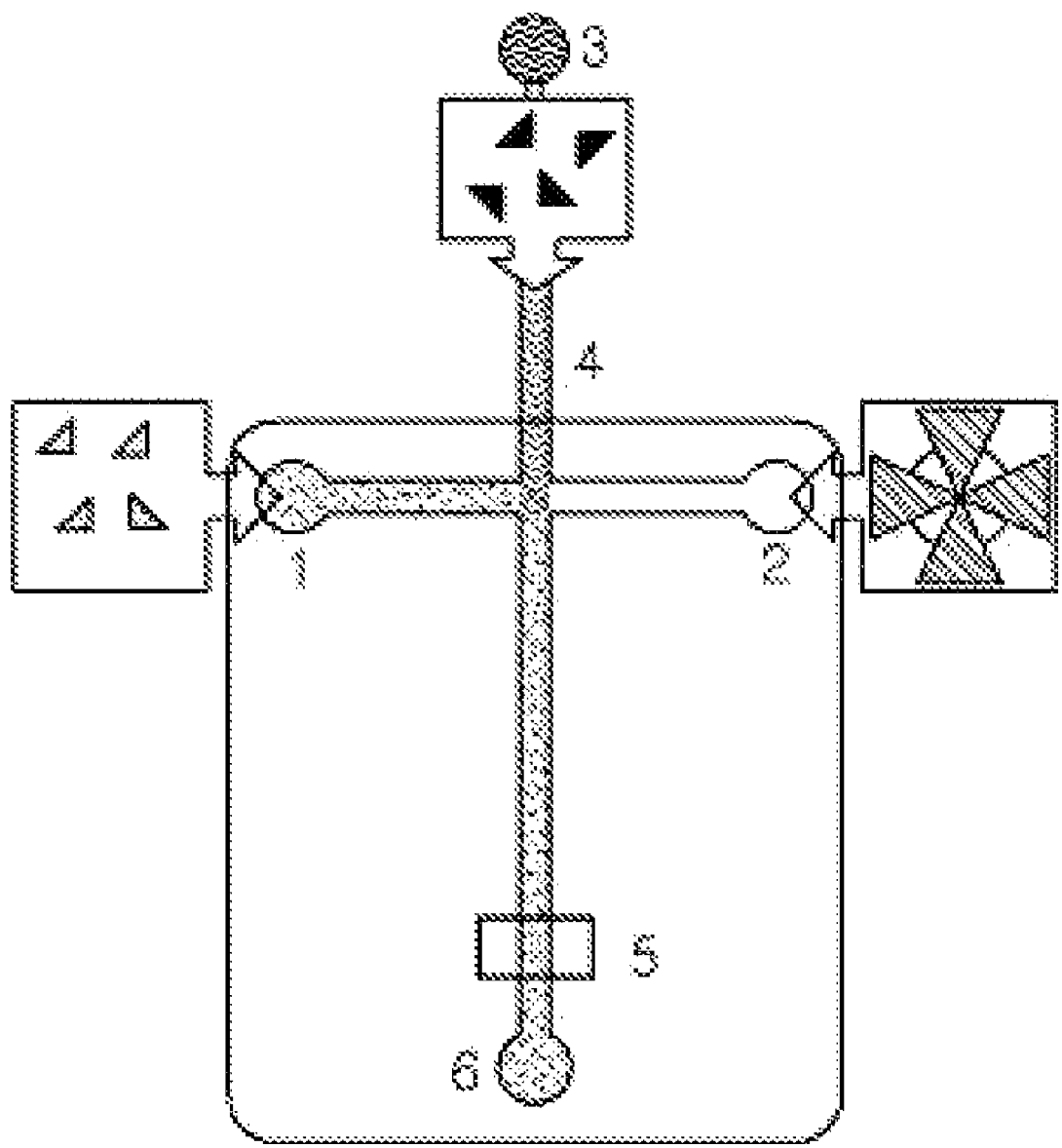
FIG. 3A is a diagram showing a configuration of the microchannel of the lab-on-a-chip in accordance with another embodiment of the invention and FIG. 3B is a forecast diagram for signals to be measured at a detection point of the microchannel.
Figure 3B:
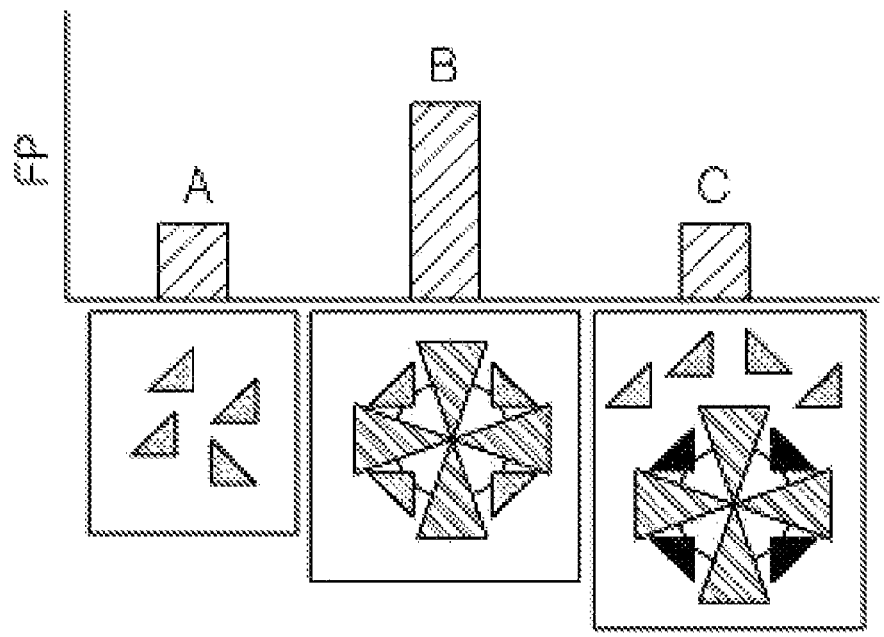

Fluorescence polarization FP for the complex of biotin and streptavidin in a lab-on-a-chip was measured using the apparatus of FIG. 2, wherein the optical chopper was not inserted. In this Embodiment, a lab-on-a-chip made of glass and composed of a microchannel having a depth of 12 μm and a width of 79 um was used instead of the 100 μL cuvette. After filling 100 μM of tetramethylrhodamine TMR solution in the microchannel of the lab-on-a-chip using a vacuum pump, a G-factor value was obtained in the same manner described above in Embodiment 1. Then, for the measurement, the samples were filled in reservoirs 1 and 2 of the lab-on-a-chip as depicted in FIG. 3A as following three cases: (A) wherein 1.25 μM of tetramethylrhodamine TMR was filled in the reservoir 1; (B) wherein 1.25 μM of TMR-biotin was put into the reservoir 1;

and (C, D and E) wherein 10 μM of TMR-biotin and 2.5 μM of streptavidin were filled, respectively, in the reservoirs 1 and 2. Subsequently, the above samples filled in the reservoirs 1 and 2 were injected into the microchannel using the vacuum pump 6 of the lab-on-a-chip to measure fluorescence polarizations FP for the samples at a detection point 5 of the lab-on-a-chip.

Figure 6A:
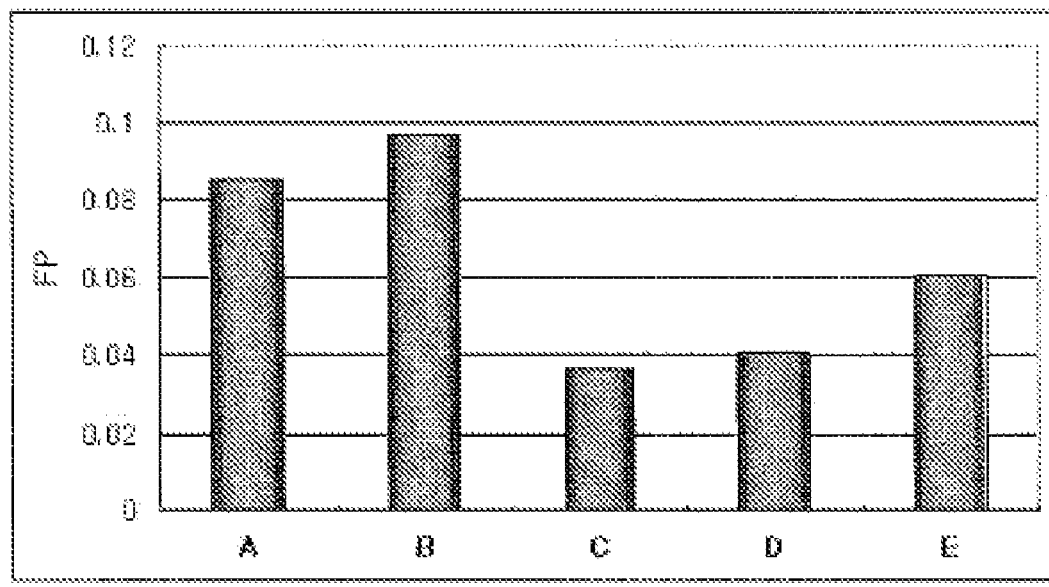
FIG. 6A is a graph showing fluorescence polarization FP for binding of fluorescently labeled biomaterials with biomolecules measured in a microchannel of a lab-on-a-chip made of glass by the apparatus of FIG. 2, wherein the optical chopper is detached, in accordance with Embodiment 2 of the invention and, FIG. 6B is a graph, wherein the offset values are subtracted from the measured values of FIG. 6A.

As a result, in case of (A), fluorescence polarization was measured 0.085; in case of (B), it was 0.097; in case of (C), it was 0.036; in case of (D), it was 0.040; and in case of (E), it was 0.064, which were deviated from the expectations of increases in fluorescence polarization FP as not increased as the complex of TMR-biotin and streptavidin was formed as shown in FIG. 6A.

Figure 6B:
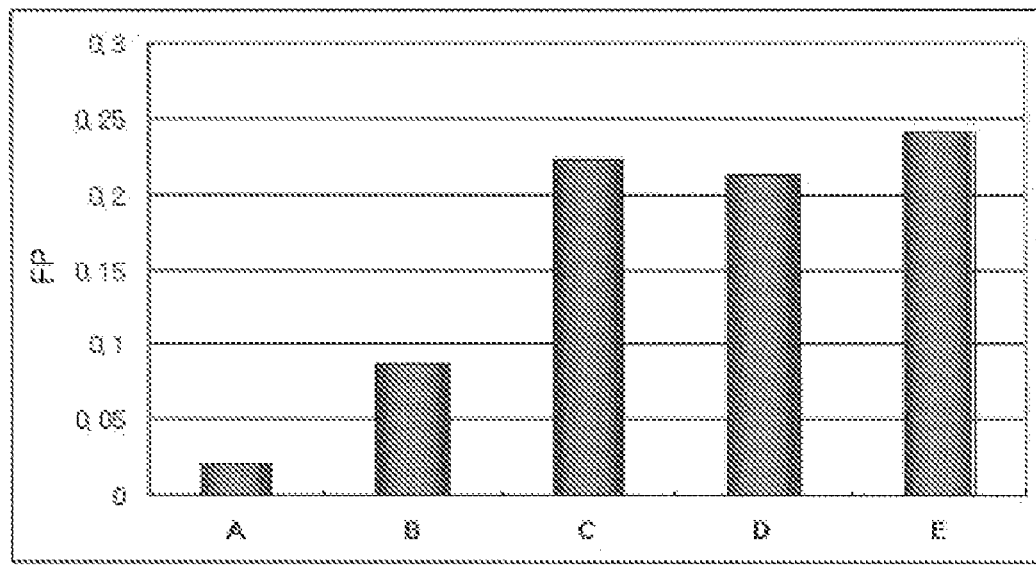

Fluorescence polarizations were recalculated from the measured values by subtracting the offset values, the offset being measured in the microchannel when only the buffer solution was filled. Consequently, in case of (A), fluorescence polarization was calculated 0.020, in case of (B), it was 0.087; in case of (C), it was 0.223; in case of (D), it was 0.212; and in case of (E), it was 0.241 as shown in FIG. 6B, which were similar to those measured in the cuvette. Accordingly, it was confirmed through repeated experiments that the measurement according to Embodiment 2 of the present invention was reproducible and had reliability.

Since the results measured by subtracting the offset according to Embodiment 2 of the invention as shown in FIG. 6B have the same patterns as those measured in Embodiment 1, it can be understood that the method and apparatus for measuring fluorescence polarization FP using the lab-on-a-chip in accordance with Embodiment 2 of the present invention complete their own objects.

Embodiment 3

Fluorescence polarization for the complex of biotin and streptavidin was measured using the apparatus of FIG. 2 including the optical chopper of the invention. In this Embodiment, a lab-on-a-chip made of glass and composed of a microchannel having a depth of 12 μm and a width of 79 μm was used to measure fluorescence polarization for a complex of biomolecule-fluorescently labeled biomaterial.

For the measurement, the samples were respectively filled in the reservoir of the lab-on-a-chip as following three cases: (A) wherein 4 μM of tetramethylrhodamine TMR was filled in the reservoir; (B) wherein 4 μM of TMR-biotin was put into the reservoir; and (C) wherein 4 μM of TMR-biotin and 1 μM of streptavidin were filled in the reservoirs.

Fluorescence polarizations FP for the above samples were measured in the microchannel of the lab-on-a-chip using the apparatus of FIG. 2 including the optical chopper.

Figure 7A:
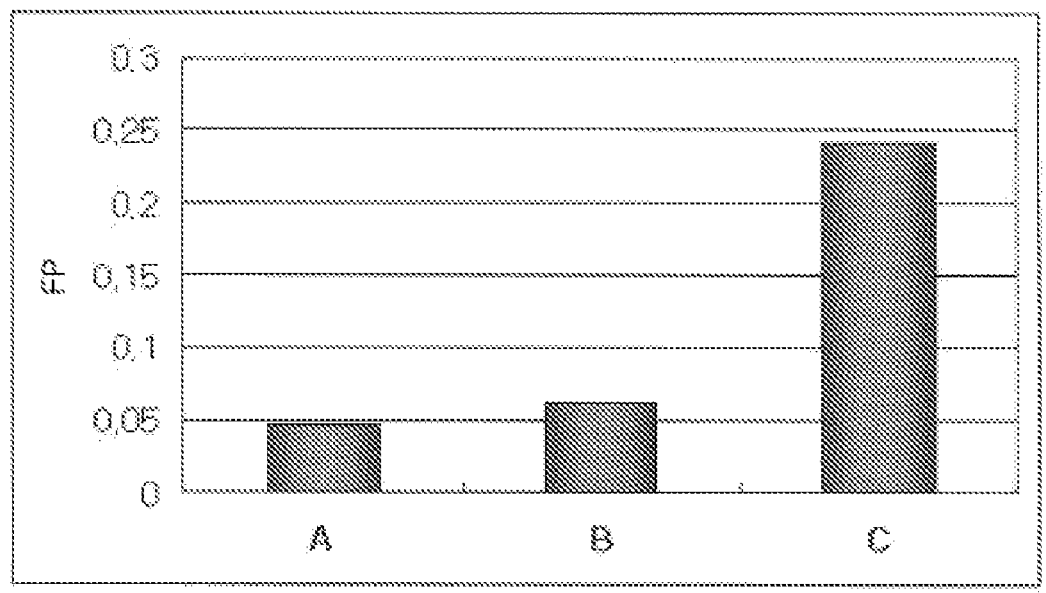
FIG. 7A is a graph showing fluorescence polarization FP for binding of fluorescently labeled biomaterials with biomolecules in a microchannel of a lab-on-a-chip made of glass measured by the apparatus of FIG. 2, wherein the optical chopper is inserted, in accordance with Embodiment 3 of the invention.

As a result, in case of (A), fluorescence polarization was measured 0.047; in case of (B), it was 0.062; and in case of (C), it was 0.240, which were increased the complex of TMR-biotin and streptavidin was formed as shown in FIG. 7A.

It was observed that the fluorescence polarization FP values were increased with the complex formation when measured using the optical chopper which improves the signal-to-noise ratio by removing the offset signals.

Figure 7B:
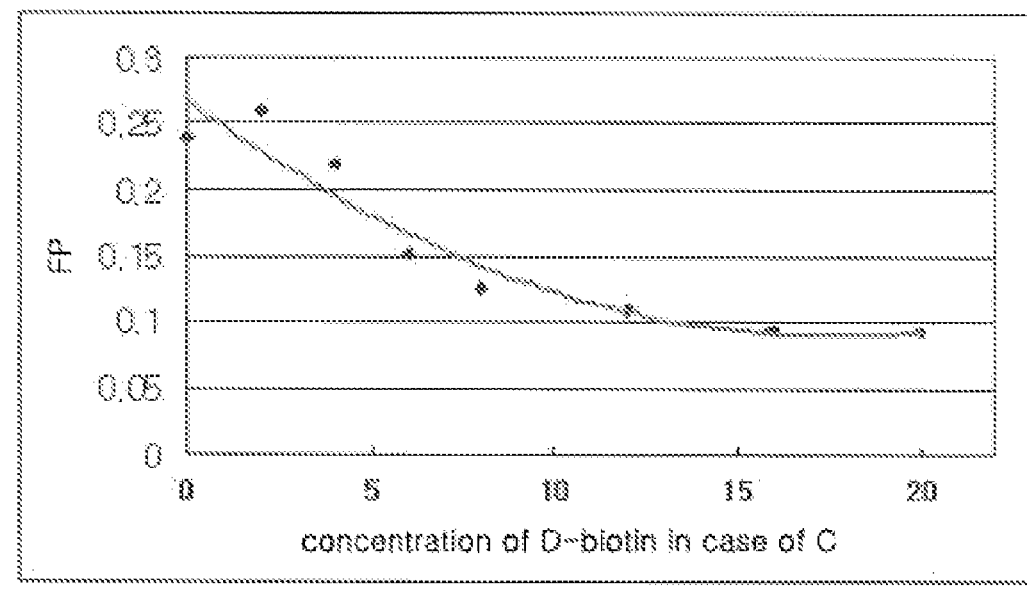
FIG. 7B is a graph showing fluorescence polarization FP for competitive inhibitions of binding between TMR-biotin and streptavidin by increasing concentrations of D-biotin.

Moreover, it was confirmed that fluorescence polarization was decreased with the increasing concentrations of D-biotin as shown in FIG. 7B because D-biotin worked as an inhibitor that caused a competing reaction, supplied from the well plate 3 of the lab-on-a-chip in FIG. 3A to the complex C in the microchannel by a capillary supplier 5.

Since the results measured using the optical chopper that removes the offset according to Embodiment 3 of the invention as shown in FIG. 7A have the same patterns as those measured in Embodiments 1 and 2, it can be understood that the method and apparatus for measuring fluorescence polarization FP using the lab-on-a-chip in accordance with Embodiment 3 of the present invention complete their own objects. In addition, the results measured and shown in FIG. 7B in accordance with this Embodiment of the invention have proved that, in case that the formation of the complex was inhibited by the inhibitor, it is possible to detect the inhibitor using the method and apparatus for measuring fluorescence polarization FP in accordance with the present invention.

Embodiment 4

Changes of fluorescence polarization FP were measured using the method and apparatus for measuring fluorescence polarization of the present invention, employing TMR-α-casein as a substrate, composed of TMR as a fluorescent probe and α-casein, a universal protein substrate reacted with various proteases.

First, TMR-α-casein, a fluorescently labeled substrate for proteases, was prepared by applying one of the well-known methods [Analytical Biochemistry (1996) 243, 1-7] as follows.

10 mg/mL of α-casein (sigma) and 5 mg/mL of 5-carboxytetramethylrhodamine succinimidyl ester were mixed in 0.1 M sodium bicarbonate buffer solution (pH 9.0) for reaction at room temperature for two and a half hours. The resulting TMR-α-casein was purified by passing the reaction mixture over a HiTrap desalting column (Sephadex G-25 Amersham Bioscience), and used after quantitation of the amounts of protein and fluorescence.

Proteinase K, trypsin, papain and elastase were used as proteases to react at increasing concentrations. First, as a comparative example, the process that the TMR-α-casein substrate was degraded by the proteases was analyzed using a commercial fluorescence spectrometer (Perkin Elmer). Proteinase K was assayed at 0.011, 0.01 and 0.1 unit/mL; trypsin and papain were assayed at 0.1, 0.8 and 4.0 unit/mL, respectively; and elastase was assayed at 0.8, 4.0 and 8.0 unit/mL, as shown in FIGS. 9A to 9D.

Figure 8:
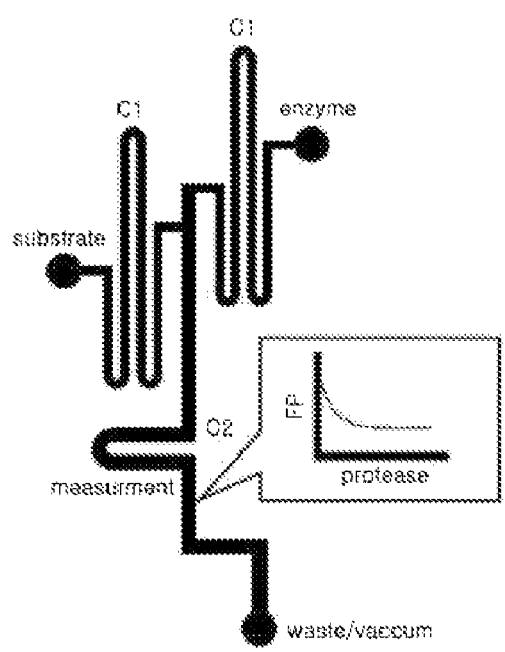
FIG. 8 is a schematic diagram depicting a configuration of a microchannel in a lab-on-a-chip for assaying the activity of proteases and a fluorescence polarization FP forecast of the assay when a protein substrate is mixed with increasing concentrations of protease, and fluorescence polarization FP is measured at a detection point in the lab-on-a-chip.
Figure 9:
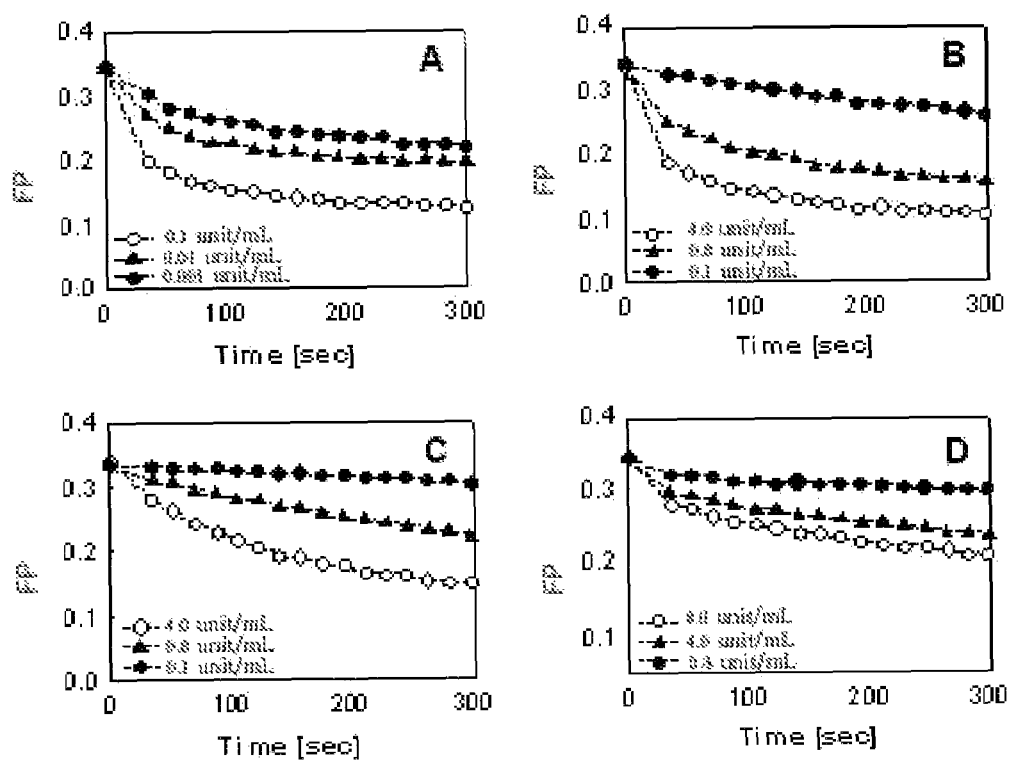
FIGS. 9A, 9B, 9C and 9D are graphs showing time courses of protease activities measured on a commercial fluorescence spectrometer by monitoring changes of fluorescence polarization FP of a TMR-α-casein substrate, derivatized with tetramethylrhodamine (TMR), with varying concentrations of enzymes such as (A) proteinase K, (B) trypsin, (C) papain and (D) elastase.
Figure 10:
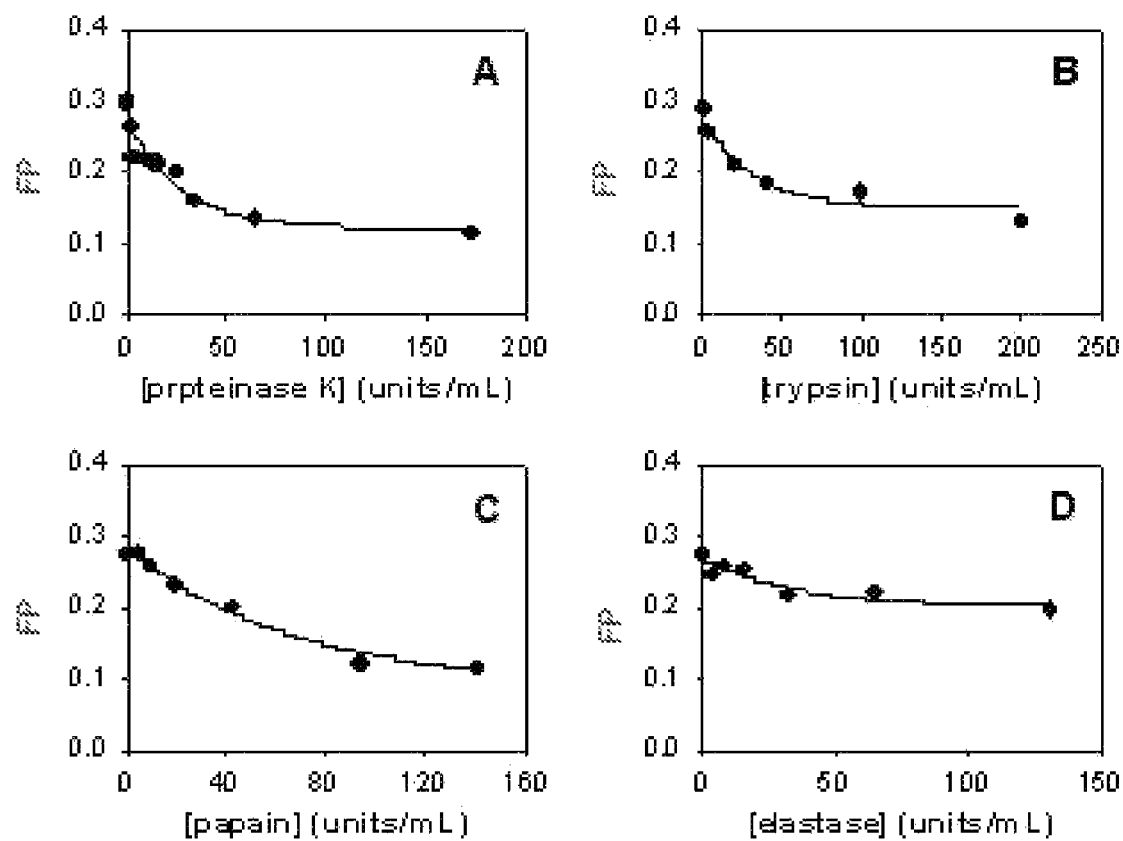
FIGS. 10A, 10B, 10C and 10D are graphs showing changes of fluorescence polarization FP for the TMR-α-casein substrate upon the reactions with enzymes such as (A) proteinase K, (B) trypsin, (C) papain and (D) elastase in the microchannel of the lab-on-a-chip of FIG. 8 measured by the apparatus of FIG. 2, wherein the optical chopper is inserted, in accordance with another embodiment of the invention.

Next, the protease assays were carried out using an apparatus for measuring fluorescence polarization including the optical chopper of FIG. 2 on a lab-on-a-chip of glass composed of a channel 1 C1, in which substrates or enzymes flowed, and a channel 2 C2, in which the reaction occurred, the channels having a depth of 12 μm and a width of 79 μm as depicted in FIG. 8.

For on-chip protease assays, the substrates and the enzymes should mix completely prior to the enzyme reactions. After checking the time required for the diffusion of TMR-α-casein in the perpendicular direction with respect to the fluid flow, it was found to take 7.4 seconds for complete mixing. Besides, the vacuum pressure used for the assays in the lab-on-a-chip was −20 kPa, and the time of fluid flow from a junction of the channel to the detection point under such conditions was 12.5 seconds. Therefore, the reaction time was confirmed to be 5.1 seconds after mixing of the substrate with the enzymes.

Subsequently, to carry out the protease assays in the lab-on-a-chip, 2 μM of TMR-α-casein (the final concentration in the channel was 1 μM) was placed in a substrate reservoir and the respective proteases were placed in an enzyme reservoir at increasing concentrations in the same manner as the comparative example. Then, the two substances were allowed to flow into a channel 2 C2, a main channel, to cause a reaction. Fluorescence polarization FP was then measured at the detection point, positioned 32 mm away from the junction, from which the substrates and the enzymes flowed in. The results were shown in FIGS. 10A to 10D.

As depicted in FIGS. 9A to 9D, it was found that fluorescence polarization values of TMR-α-casein decreased as the reaction proceeded in all cases of proteinase K (A), trypsin (B), papain (C) and elastase (D). Besides, it was noted that fluorescence polarization values decreased with increasing concentrations of the enzymes, and plateaued when the concentration of the enzymes reached at the point generating a specific rate or more. It was understood that fluorescence polarization values decreased since the volume of TMR-α-casein became smaller as it was degraded as the reaction proceeded, and the degree of reaction for a specific period became larger with the increasing enzyme concentrations.

Moreover, as depicted in FIGS. 10A to 10D, it was found that fluorescence polarization values decreased with increasing concentrations of the enzymes in all cases of proteinase K (A), trypsin (B), papain (C) and elastase (D), similarly as shown in FIGS. 9A to 9D. Again, it was noted that fluorescence polarization values plateaued when the concentration of the enzymes reached at the point generating a specific rate or more.

Furthermore, using casein, a universal protein substrate, as a substrate for the four proteases resulted in a rapid assay without the need to change the substrates suitable for the respective proteases.

According to the method and apparatus for measuring fluorescence polarization of the present invention, it is possible to enhance the sensitivity and the reliability of the measurement by improving the signal-to-noise ratio and to provide automated analyses using the lab-on-a-chip. Accordingly, it is possible to carry out analyses of interactions between biomolecules using minute amounts of samples compared to conventional methods, to detect substances that induce or inhibit the reaction, and to measure the activity or the concentration of enzymes. Furthermore, it is possible to provide rapid analyses using casein, a universal protein substrate, as a substrate for various proteases without changing the substrates suitable for the respective proteases.

What is claimed is:

1. A method for detecting a substance that induces or inhibits formation of a complex between biomolecules using a fluorescence polarization FP measuring apparatus for a microchannel, said method comprising the steps:

(1) preparing a fluorescently labeled biomaterial and a biomolecule,
   (2) injecting the fluorescently labeled biomaterial and the biomolecule into a microchannel in a lab-on-a-chip to form a complex,
   (3) causing a reaction between the complex and a sample material,
   (4) irradiating a polarized light to the resultant complex to measure fluorescence polarization FP,
   (5) quantifying the measured fluorescence polarization FP to determine the extent of fluorescence polarization, and
   (6) selecting the sample material which changes the flourescence polarization FP;

wherein the fluorescence polarization FP measuring apparatus comprises
   a polarization generation part,
   a fluorescence polarization FP separation part, and
   a fluorescence polarization FP measurement part;
wherein the polarization generation part includes:
   a laser source,
   a first filter that filters light liberated from the laser source,
   first and second mirrors that control the direction of the light passing through the first filter,
   a polarizer that polarizes the light reflected by the second mirror,
   a beam splitter that splits the polarized light passing through the polarizer, and
   a lens that collimate the polarized light to a sample material in the microchannel;
wherein the fluorescence polarization FP separation part includes:
   a lens that collects fluorescence emitted by excited fluorescently labeled biomaterials by polarized light irradiated from the polarization generation part,
   a third mirror that controls the direction of the fluorescence passing through the lens,
   a second filter that filters the fluorescence reflected by the third mirror, and
   a polarized beam splitter that splits the fluorescence passing through the second filter; and
wherein the fluorescence polarization FP measurement part includes:
   a third filter that filters the fluorescence passing through the polarized beam splitter,
   vertical and horizontal photomultiplier tubes (PMTs) that measure fluorescence signals of the emitted light passing through the third filter in vertical and horizontal planes,
   a polarizer installed in front of the horizontal PMT, and
   an oscilloscope that measures the fluorescence polarization FP passing through the photomultiplier tubes.

2. The method as recited in claim 1, wherein an optical chopper for turning on/off the light source between the first filter and the first mirror to enhance a signal-to-noise ratio is interposed.

3. The method as recited in claim 1, wherein the microchannel has a width of 10 μm to 100 μm.

4. The method as recited in claim 1, wherein in step (2) the fluorescently labeled substrate and the sample meet in a main channel of the lab-on-a-chip via a microfluidic control by pressure gradient generated using a vacuum pump coupled to reactant reservoirs.

5. The method as recited in claim 1, wherein in step (3) after obtaining a G-factor value, which is a compensation value of a fluorometer and a light source for a specific fluorescent probe in the microchannel when a polarizer is not attached, the polarizer is inserted in path of excitation to irradiate a polarized light to a biomolecule-fluorescently labeled biomaterial complex in the microchannel and, then fluorescence passes through vertical and horizontal photomultiplier tubes, thus obtaining measured values of fluorescence; and in step (4) fluorescence polarization FP is determined from the G-factor value and the measured values.

6. The method as recited in claim 1, wherein the method is applied to quantitative measurements for interactions between biomolecules.

7. A method for measuring activity or concentration of an enzyme using a fluorescence polarization FP measuring apparatus for a microchannel, said method comprising the steps:

(1) preparing a fluorescently labeled substrate and a sample,
   (2) injecting the fluorescently labeled substrate and the sample into a microchannel in a lab-on-a-chip to form a complex,
   (3) irradiating a polarized light to the resultant complex to measure fluorescence polarization FP, and (4) quantifying the measured fluorescence polarization FP to determine activity or concentration of the enzyme;

wherein the fluorescence polarization FP measuring apparatus comprises
- a polarization generation part,
- a fluorescence polarization FP separation part, and
- a fluorescence polarization FP measurement part;

wherein the polarization generation part includes:
- a laser source,
- a first filter that filters light liberated from the laser source,
- first and second mirrors that control the direction of the light passing through the first filter,
- a polarizer that polarizes the light reflected by the second mirror,
- a beam splitter that splits the polarized light passing through the polarizer, and
- a lens that collimate the polarized light to a sample material in the microchannel;

wherein the fluorescence polarization FP separation part includes:
- a lens that collects fluorescence emitted by excited fluorescently labeled biomaterials by polarized light irradiated from the polarization generation part,
- a third mirror that controls the direction of the fluorescence passing through the lens,
- a second filter that filters the fluorescence reflected by the third mirror, and
- a polarized beam splitter that splits the fluorescence passing through the second filter; and wherein the fluorescence polarization FP measurement part includes:
- a third filter that filters the fluorescence passing through the polarized beam splitter,
- vertical and horizontal photomultiplier tubes (PMTs) that measure fluorescence signals of the emitted light passing through the third filter in vertical and horizontal planes,
- a polarizer installed in front of the horizontal PMT, and
- an oscilloscope that measures the fluorescence polarization FP passing through the photomultiplier tubes.

8. The method as recited in claim 7, wherein an optical chopper for turning on/off the light source between the first filter and the first mirror to enhance a signal-to-noise ratio is interposed.

9. The method as recited in claim 7, wherein the microchannel has a width of 10 μm to 100 μm.

10. The method as recited in claim 7, wherein in step (2) the fluorescently labeled substrate and the sample meet in a main channel of the lab-on-a-chip via a microfluidic control by pressure gradient generated using a vacuum pump coupled to reactant reservoirs.

11. The method as recited in claim 7, wherein in step (3) after obtaining a G-factor value, which is a compensation value of a fluorometer and a light source for a specific fluorescent probe in the microchannel when a polarizer is not attached, the polarizer is inserted in path of excitation to irradiate a polarized light to a biomolecule-fluorescently labeled biomaterial complex in the microchannel and, then fluorescence passes through vertical and horizontal photomultiplier tubes, thus obtaining measured values of fluorescence; and in step (4) fluorescence polarization FP is determined from the G-factor value and the measured values.

12. The method as recited in claim 7, wherein the method is applied to quantitative measurements for interactions between biomolecules.

* * * * *